United States Patent
Cox et al.

(10) Patent No.: US 12,036,229 B2
(45) Date of Patent: Jul. 16, 2024

(54) USE OF PHOSPHORYLATED HEPTOSE COMPOUNDS

(71) Applicants: NATIONAL RESEARCH COUNCIL OF CANADA, Ottawa (CA); THE GOVERNING COUNCIL OF THE UNIVERSITY OF TORONTO, Toronto (CA)

(72) Inventors: Andrew Cox, Ottawa (CA); Janelle Sauvageau, Ottawa (CA); Scott Gray-Owen, Oakville (CA); Xinyi Guo, North York (CA)

(73) Assignees: National Research Council of Canada, Ottawa (CA); The Governing Council of the University of Toronto, Toronto (CA)

( * ) Notice: Subject to any disclaimer, the term of this patent is extended or adjusted under 35 U.S.C. 154(b) by 583 days.

(21) Appl. No.: 16/612,284

(22) PCT Filed: May 11, 2018

(86) PCT No.: PCT/CA2018/000091
§ 371 (c)(1),
(2) Date: Feb. 3, 2020

(87) PCT Pub. No.: WO2018/205010
PCT Pub. Date: Nov. 15, 2018

(65) Prior Publication Data
US 2020/0268774 A1   Aug. 27, 2020

Related U.S. Application Data

(60) Provisional application No. 62/504,774, filed on May 11, 2017.

(51) Int. Cl.
| | |
|---|---|
| A61K 31/70 | (2006.01) |
| A61K 39/39 | (2006.01) |
| A61P 31/04 | (2006.01) |
| A61P 31/18 | (2006.01) |
| A61P 35/00 | (2006.01) |
| A61K 39/00 | (2006.01) |
| A61K 45/06 | (2006.01) |

(52) U.S. Cl.
CPC .............. *A61K 31/70* (2013.01); *A61K 39/39* (2013.01); *A61P 31/04* (2018.01); *A61P 31/18* (2018.01); *A61P 35/00* (2018.01); *A61K 2039/55583* (2013.01); *A61K 45/06* (2013.01)

(58) Field of Classification Search
None
See application file for complete search history.

(56) References Cited

FOREIGN PATENT DOCUMENTS

| WO | 2011038186 A1 | 3/2011 |
|---|---|---|
| WO | 2016054745 A1 | 4/2016 |

OTHER PUBLICATIONS

Zamyatina et al (Efficient chemical synthesis of both anomers of ADP L-glycero- and D-glycero-D-manno-heptopyranose. Carbohydrate Research 338 (2003) 2571-2589) (Year: 2003).*
Malott et al (Neisseria gonorrhoeae-derived heptose elicits an innate immune response and drives HIV-1 expression. Proceedings of the National Academy of Sciences of the United States of America. vol. 110, No. 25. Jun. 18, 2013, pp. 10234-10239) (Year: 2013).*
Deeks (Shock and kill. Nature. vol. 487 (2012) p. 439-440) (Year: 2012).*
Zamyatina, A., et al., "Efficient chemical synthesis of both anomers of ADP L-glycero- and D-glycero-D-manno-heptopyranose," Carbohydrate Research, 2003, vol. 338; pp. 2571-2589; Institute of Chemistry, University of Agricultural Sciences, Muthgasse 18, A-1190 Vienna, Austria.
Gaudet, R., et al., "Cytosolic detection of the bacterial metabolite HBP activates TIFA-dependent innate immunity," Science, sciencemag. org, 2015, vol. 348: Issue 6240; pp. 1251-1255. American Association for the Advancement of Science, 1200 New York Avenue NW, Washington, DC 20005.
Malott, R., et al.,"Neisseria gonorrhoeae-derived heptose elicits an innate immune response and drives HIV-1 expression," Proceedings of the National Academy of Sciences of the United States of America, 2013; vol. 110: No. 25; pp. 10234-10239.
Medzhitov, R., et al., "Recognition of microorganisms and activation of the immune response," Nature, 2007, vol. 449: No. 18; pp. 819-826; Nature Publishing Group.
Medzhitov, R., et al., "Approaching the Asymptote: 20 Years Later," Immunity Perspective, 2009, vol. 30: Issue 6; pp. 766-775.
Robinson, J., and Moehle, K., "Structural aspects of molecular recognition in the immune system. Part II: Pattern recognition receptors," Pure Appl. Chem. 2014 86(10): 1483-1538.
International Search Report and Written Opinion for International Patent Application No. PCT/CA2018/00091, mailed Jul. 17, 2018, 11 pages.
Adekoya et al., 2018, d-Glycero-β-d-Manno-Heptose 1-Phosphate and d-Glycero-β-d-Manno-Heptose 1,7-Biphosphate are Both Innate Immune Agonists, *J Immunol.*, 201(8):2385-2391. Epub Sep. 17, 2018.
Gaudet et al., 2015, Innate Immunity. Cytosolic detection of the bacterial metabolite HBP activates TIFA-dependent innate immunity, *Science*, 348(6240):1251-5.

(Continued)

*Primary Examiner* — Jake M Vu
(74) *Attorney, Agent, or Firm* — Banner & Witcoff LLP

(57) ABSTRACT

Phosphorylated heptose compounds are useful in modulating an immune response in a subject. Also, the compounds are useful as adjuvants.

3 Claims, 14 Drawing Sheets

(56) References Cited

OTHER PUBLICATIONS

Gaudet et al., 2015, Supplementary Materials for: Cytosolic detection of the bacterial metabolite HBP activates TIFA-dependent innate immunity, *Science*, 348(6240):1251-5. www.sciencemag.org/content/348/6240/1251/supl/DC1 <http://www.sciencemag.org/content/348/6240/1251/supl/DC1>.

Kim et al., 2022, Latency reversal plus natural killer cells diminish HIV reservoir in vivo, *Nat Commun*, 13: 121. <https://doi.org/10.1038/s41467-021-27647-0>.

Malott et al., 2013, Supporting Information, 10.1073/pnas.1303738110. <http://www.pnas.org/lookup/suppl/doi:10.1073/pnas.1303738110/-/DCSupplemental>.

\* cited by examiner

A) Belongs to compound JS7

B) Belongs to compound JS7

C) Belongs to compound JS7

A) Proton spectra of JS8

USE OF PHOSPHORYLATED HEPTOSE COMPOUNDS

This application claims the benefit of U.S. Provisional Patent Application Ser. No. 62/504,774 filed on May 11, 2017. The content of the U.S. Provisional patent application is incorporated herein in its entirety by reference.

FIELD OF THE INVENTION

The present invention relates generally to phosphorylated heptose compounds. More specifically, the present invention relates to use of heptopyranose phosphates in modulating an immune response in a subject.

BACKGROUND OF THE INVENTION

An ability to modulate the immune system is becoming more and more critical as we strive to improve the immune response of individuals in order to generate a protective response, e.g. in immunocompromised individuals including cancer patients. This is outlined for example in WO 2016/054745 entitled "Methods of modulating immune system responses."

Pathogen associated molecular patterns (PAMPs) are molecules produced by pathogens that are specifically recognised by the human immune system in order to generate innate and adaptive immune responses to keep foreign pathogens at bay. The ability to synthesise PAMP's will enable the specific modulation of the immune system to improve the immune response and generate protection.

Only a limited number of PAMPs have been identified, e.g. lipopolysaccharide (LPS), DNA and flagellin. This limits the opportunity to investigate the immunomodulatory properties of these molecules. In most cases PAMPs are difficult to synthesise or isolate and thus precludes an opportunity to specifically address how these PAMP's interact with the immune system in order to exploit this relationship as a pure, fully characterised supply of the PAMPs is unavailable.

The inventors are also aware of the documents [1] to [5]. There is a need to identify novel PAMP molecules.

SUMMARY OF THE INVENTION

The inventors have identified phosphorylated heptose compounds useful in modulating an immune response in a subject. Also, the compounds are useful as adjuvants.

More specifically, in accordance with aspects of the invention, there is provided the following:

(1) Use of an effective amount of D-glycero-D-manno-heptopyranose 1β-phosphate (JS7 or HMP-β), for modulating an immune response in a subject.

(2) A method of modulating an immune response in a subject, comprising using an effective amount of D-glycero-D-manno-heptopyranose 1β-phosphate (JS7 or HMP-β).

(3) A use according to (1) above or a method as defined in (2) above, wherein the immune response of the subject is enhanced.

(4) A use according to (1) above or a method as defined in (2) above, further comprising use of an immunogen.

(5) A use or method according to (4) above, wherein the immunogen is in a vaccine composition.

(6) A use or method according to (4) above, wherein the immunogen is an antigen derived from a bacterial virus or pathogen.

(7) A use according to (1) above or a method according to (2) above, comprising treating or preventing a bacterial, viral or parasitic infection.

(8) A use according to (1) above or a method according to claim, comprising treating or preventing a bacterial by Gram-negative bacteria.

(9) A use according to (1) above or a method according to (2) above, comprising treating or preventing a bacterial by Gram-positive bacteria.

(10) A use or method according to (8) above, wherein the Gram-negative bacteria are selected from the group of bacteria consisting of *Neisseria, Escherichia, Klebsiella, Salmonella, Shigella, Vibrio, Helicobacter, Pseudomonas, Burkholderia, Haemophilus, Moraxella, Bordetella, Francisella, Pasteurella, Borrelia, Campylobacter, Yersinia, Rickettsia, Treponema, Chlamydia* and *Brucella*.

(11) A use or method according to (9) above, wherein the Gram-positive bacteria are selected from the group of bacteria consisting of *Staphylococcus, Streptococcus, Listeria, Corynebacterium, Enterococcus, Clostridium* and *Mycobacterium*.

(12) A use according to (1) above or a method according to (2) above, comprising treating Human Immunodeficiency virus (HIV).

(13) A use or method according to (12) above, wherein the use of JS7 or HMP-β induces HIV gene expression from latently infected cells.

(14) A use or method according to (7) above, wherein the parasitic infection is caused by a parasite selected from the group of parasites consisting of *Leishmania, Plasmodium, Toxoplasma, Trypanosoma* and *Schistosoma*.

(15) A use as according to (1) above or a method according to (2) above, comprising treating a cancer.

(16) A use according to (1) above or a method according to (2) above, comprising a direct use of JS7 or HMP-β on cancer cells.

(17) Use of an effective amount of D-glycero-D-manno-heptopyranose 1β-phosphate (JS7 or HMP-β), for treating Human Immunodeficiency Virus (HIV) in a subject.

(18) A method for treating Human Immunodeficiency Virus (HIV) in a subject, comprising administering to the subject an effective amount of D-glycero-D-manno-heptopyranose 1β-phosphate (JS7 or HMP-β).

(19) A use according to (17) or a method according to claim 18, wherein the use or administration of JS7 or HMP-β induces HIV gene expression from latently infected cells.

(20) Use of an effective amount of D-glycero-D-manno-heptopyranose 1β-phosphate (JS7 or HMP-β), for treating cancer in a subject.

(21) A method for treating cancer in a subject, comprising administering to the subject an effective amount of D-glycero-D-manno-heptopyranose 1β-phosphate (JS7 or HMP-β).

(22) A use according to (1) or a method according to claim 2, comprising preventing, treating, ameliorating, or inhibiting an injury, disease, disorder or condition wherein modulation of the immune response is beneficial.

(23) Use of an effective amount of D-glycero-D-manno-heptopyranose 1β-phosphate (JS7 or HMP-β) as an adjuvant, in a subject.

(24) Use, in combination with an immunogen, of an effective amount of D-glycero-D-manno-heptopyranose 1β-phosphate (JS7 or HMP-β) as an adjuvant, in a subject.

(25) A method of modulating an immune response in a subject, comprising administering to the subject an effective amount of D-glycero-D-manno-heptopyranose 1β-phosphate (JS7 or HMP-β) as an adjuvant.

(26) A method of modulating an immune response in a subject, comprising administering to the subject, in combination with an immunogen, of an effective amount of D-glycero-D-manno-heptopyranose 1β-phosphate (JS7 or HMP-β) as an adjuvant.

(27) A use according to (24) or a method according to (26), wherein the immunogen is in a vaccine composition.

(28) A use according to (24) or a method according to (26), wherein the immunogen is an antigen derived from a bacterial virus or pathogen.

(29) Use, in the treatment or prevention of a medical condition in a subject, of an effective amount of D-glycero-D-manno-heptopyranose 1β-phosphate (JS7 or HMP-β) as an adjuvant.

(30) A method of treating or preventing a medical condition in subject, comprising administering to the subject an effective amount of D-glycero-D-manno-heptopyranose 1β-phosphate (JS7 or HMP-β) as an adjuvant.

(31) A use according to (29) or method according to (30), wherein the use or administration of JS7 or HMP-β is in combination with a therapeutic agent for the medical condition.

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

In the Appended Drawings:

FIG. 14a. Tumours were measured daily over time. FIG. 14b. Tumor sizes were established on D10 post CT26 injection. FIG. 14c. Mice were injected intraperitoneally with either LPS (1× at 3 mg/kg), HMP (200 μg per day for 3 days in a row at D10, D11, D12), or PBS (1x per day for 3 days in a row). Changes in tumour volume were measured daily relative to day 10 as displayed. Data was analysed by 2-way ANOVA with Dunnett's multiple comparison.

DESCRIPTION OF ILLUSTRATIVE EMBODIMENTS

Figure 1:
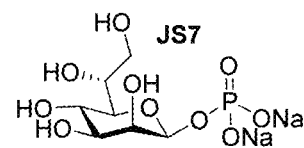
FIG. 1: A) $^1$H NMR of D-glycero-D-manno-heptopyranose 1β-phosphate (JS7 or HMP-3) B) $^{13}$C NMR of compound JS7 or HMP-β C) $^{31}$P NMR of compound JS7 or HMP-β.
Figure 1:
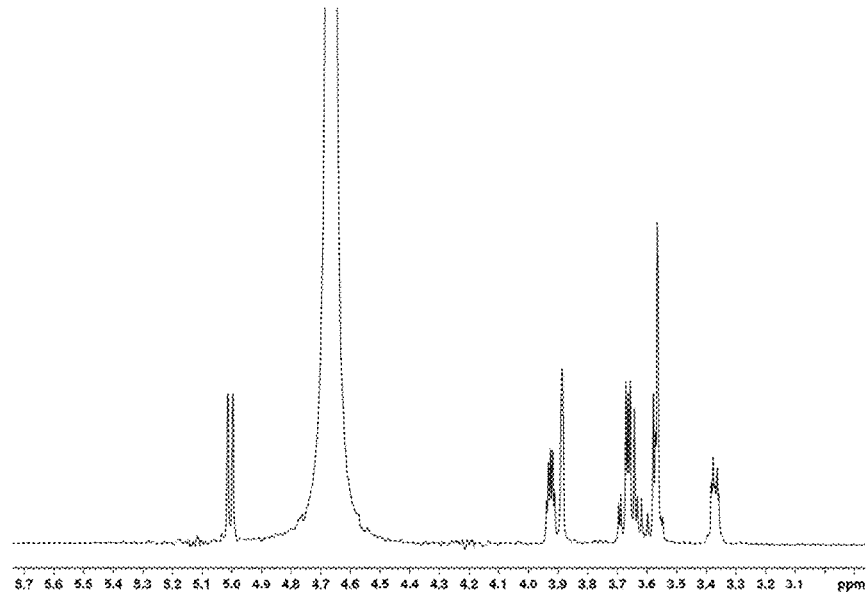
Figure 1:
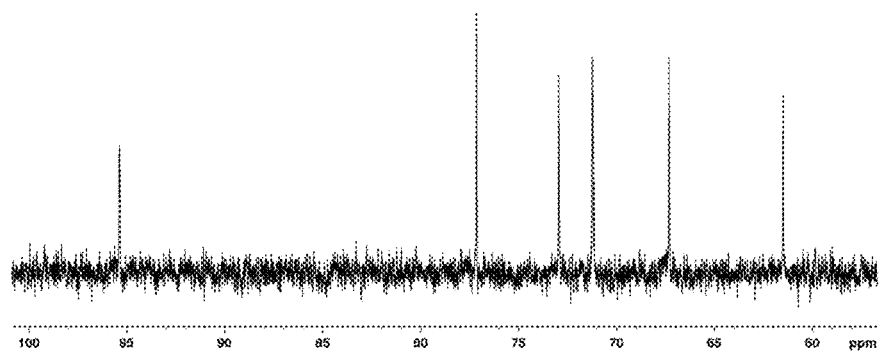
Figure 1:
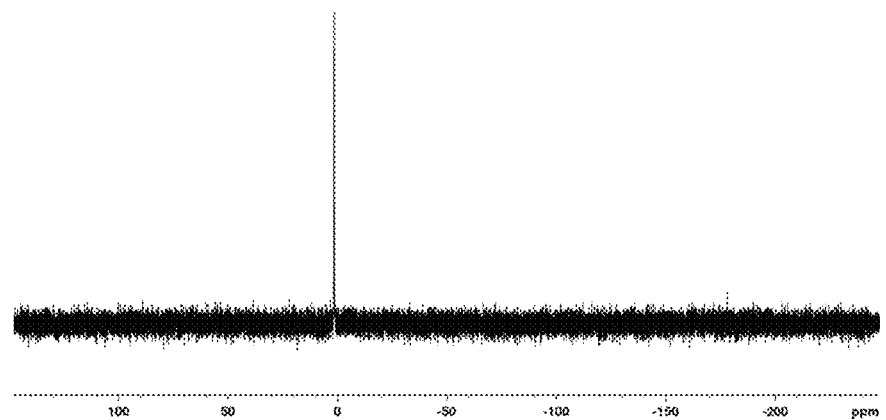

Before the present invention is further described, it is to be understood that the invention is not limited to the particular embodiments described below, as variations of these embodiments may be made and still fall within the scope of the appended claims. It is also to be understood that the terminology employed is for the purpose of describing particular embodiments, and is not intended to be limiting. Instead, the scope of the present invention will be established by the appended claims.

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this invention pertains.

In general, the methods of the present disclosure may be used to therapeutically or prophylactically treat any subjects for which increased activation of the immune system or an altered immune response would be beneficial. This includes, but is not restricted to a subject suffering from a condition which deleteriously affects the immune system, including any subjects at a heightened risk of infection or actually infected, for example due to surgery or imminent surgery, injury, illness, radiation or chemotherapy, and any subjects suffering from autoimmune diseases, inflammatory disorders, cancers, and diseases which cause the normal metabolic immune response to be compromised, such as HIV (AIDS).

As used herein, the term "phosphorylated heptose compound" refers a monosaccharide with seven carbon atoms, wherein at least one hydroxyl group is replaced by a group comprising a phosphorus atom. For example, the term "mono-phosphorylated heptose compound" refers a monosaccharide with seven carbon atoms, wherein one hydroxyl group is replaced by a group comprising a phosphorus atom. The term also refers to a derivative or an analogue of such compound.

As used herein, the term "modulate" in connection with an immune or inflammatory response refers to a qualitative or quantitative alteration in the immune or inflammatory response in a subject.

As used herein, the term "vaccine" or "vaccine composition" refers to a pharmaceutical composition containing an immunogen. The composition may be used for modulating an immune response in a subject. The term also refers to subunit vaccines, i.e., vaccine compositions containing immunogens which are separate and discrete from a whole organism with which the immunogen is associated in nature.

The term "adjuvant" as used herein in relation to the compound of the invention, refers to the compound serving as enhancer of the effectiveness of a medical treatment and/or enhancer of the immune response to an antigen, in a subject.

As used herein, the term "effective amount" refers to the amount of a compound or reaction product sufficient to cure, alleviate or partially arrest the clinical manifestations of a given disease and its complications in a therapeutic intervention comprising the administration of said compound or reaction product. An effective amount for each purpose will depend on the severity of the disease or injury as well as the weight and general state of the subject.

As used herein, the term "subject" is understood as being any mammal including a human being treated with a compound of the invention.

As used herein the terms "treatment" and "treating" mean the management and care of a subject for the purpose of combating a condition, such as a disease or disorder. The term is intended to include the full spectrum of treatments for a given condition from which the patient is suffering, such administration of the active compounds to alleviate the symptoms or complications, to delay the progression of the condition, and/or to cure or eliminate the condition. The subject to be treated is preferably a mammal, in particular a human being.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The inventors have identified phosphorylated heptose compounds useful in modulating an immune response in a subject. Also, the compounds are useful as adjuvants.

The present invention is illustrated in further details by the following non-limiting examples.

D-glycero-D-manno-heptopyranose 1β-phosphate (JS7 or HMP-β), chemical structure below, was synthesized as described by Zamyatina et al. [6]. The spectra obtained (FIG. 1) are in accordance with the literature data. The sole difference in the synthesis of the compound was that the compound was dissolved in brine and eluted through a G-15 column to exchange the trimethylamine salt for sodium.

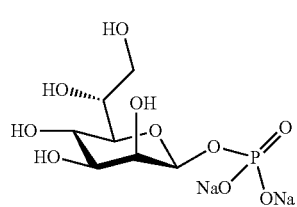

JS7 or HMP-β

Figure 4:
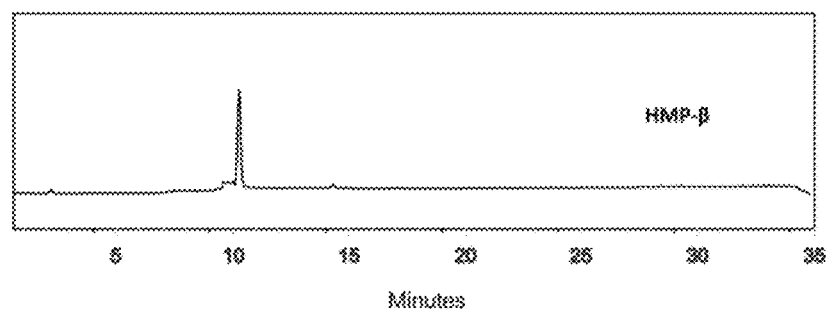
FIG. 4: Purity of HBP JS7 or HMP-β. Chromatogram of JS7 or HMP-β. Detector: PAD, Column: Carbopac™ Solvent A: NaOH, 0.1M, Solvent B: AcONa, 1M and NaOH 0.05M, Conditions: 0-100% B in 30 minutes and 100% solvent B for 5 minutes.

An HPLC analysis shows that compound JS7 or HMP-β is pure; see FIG. 4.

Figure 2:
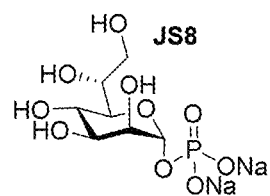
FIG. 2: A) $^1$H NMR of D-glycero-D-manno-heptopyranose 1α-phosphate (JS8 or HMP-α).
Figure 2:
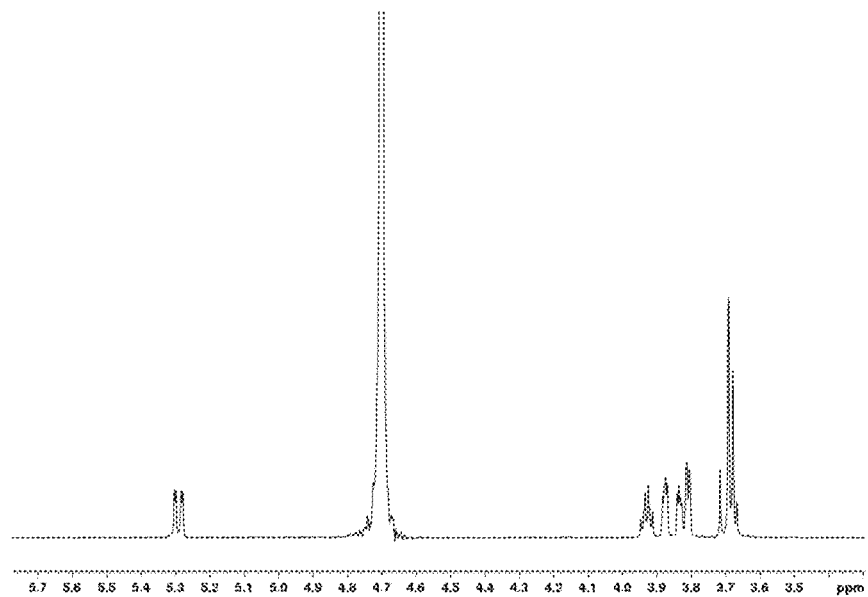

D-glycero-D-manno-heptopyranose 1α-phosphate (JS8 or HMP-α), chemical structure below, was synthesized as described by Zamyatina et al. [6]. The spectrum obtained (FIG. 2) is in accordance with the literature data. The sole difference in the synthesis of the compound was that the compound was dissolved in brine and eluted through a G-15 column to exchange the trimethylamine salt for sodium.

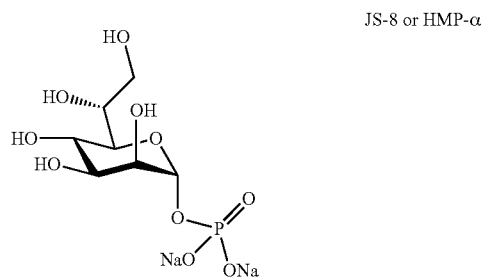

JS-8 or HMP-α

Figure 5:
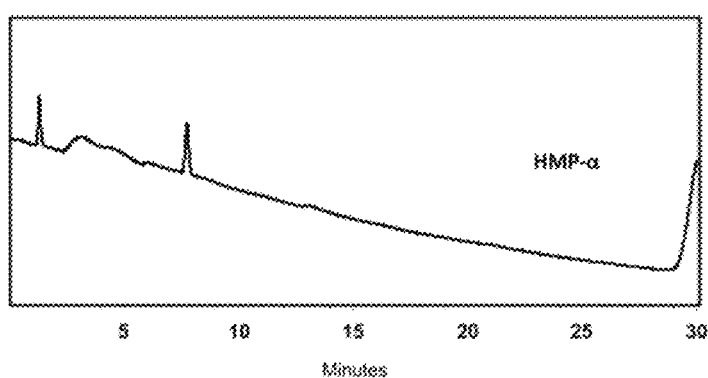
FIG. 5: Purity of JS8 or HMP-α. Chromatogram of JS8 or HMP-α. Detector: PAD, Column: Carbopac™ Solvent A: NaOH, 0.1M, Solvent B: AcONa, 1M and NaOH 0.05M, Conditions: 0-100% B in 30 minutes.

An HPLC analysis shows that compound JS8 or HMP-α is pure; see FIG. 5.

Figure 3:
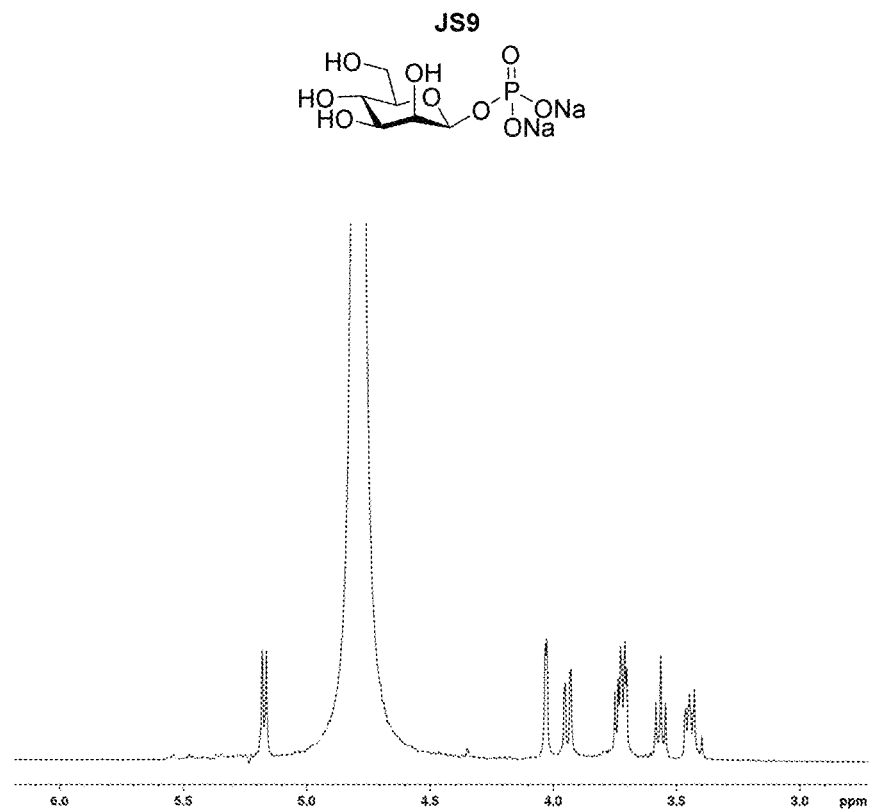
FIG. 3: A) $^1$H NMR of D-mannose 1β-phosphate (JS9 or Man-1β-P).

D-mannose 1β-phosphate (JS9 or Man-1β-P), chemical structure below, was synthesized as described by Zamyatina et al. [6], however starting from acetylated D-mannose instead of acetylated heptose and purifying in brine and eluting through a G-15 column to exchange the trimethylamine salt for sodium. The spectrum obtained (FIG. 3) is in accordance with the literature data [7].

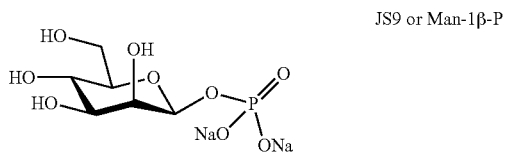

JS9 or Man-1β-P

Figure 6:
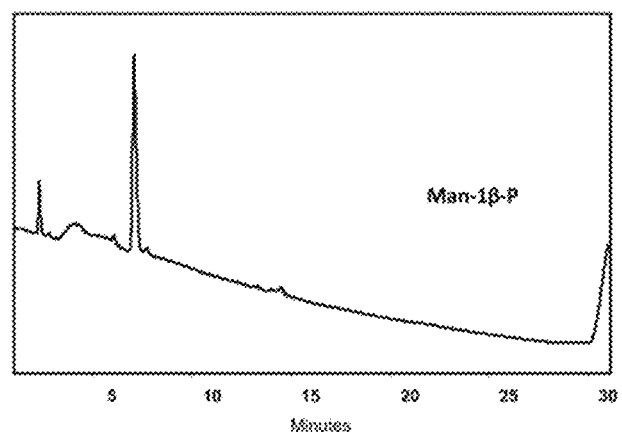
FIG. 6: Purity of JS9 or Man-1β-P. Chromatogram of JS9 or Man-1β-P. Detector: PAD, Column: Carbopac™ Solvent A: NaOH, 0.1M, Solvent B: AcONa, 1M and NaOH 0.05M, Conditions: 0-100% B in 30 minutes.

An HPLC analysis shows that compound JS9 or Man-1β-P is pure; see FIG. 6.

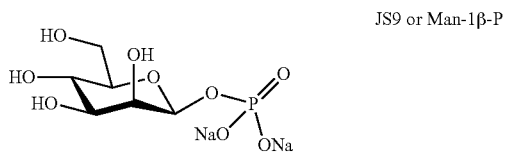

JS9 or Man-1β-P

Biological Experiments

Example 1

Figure 7:
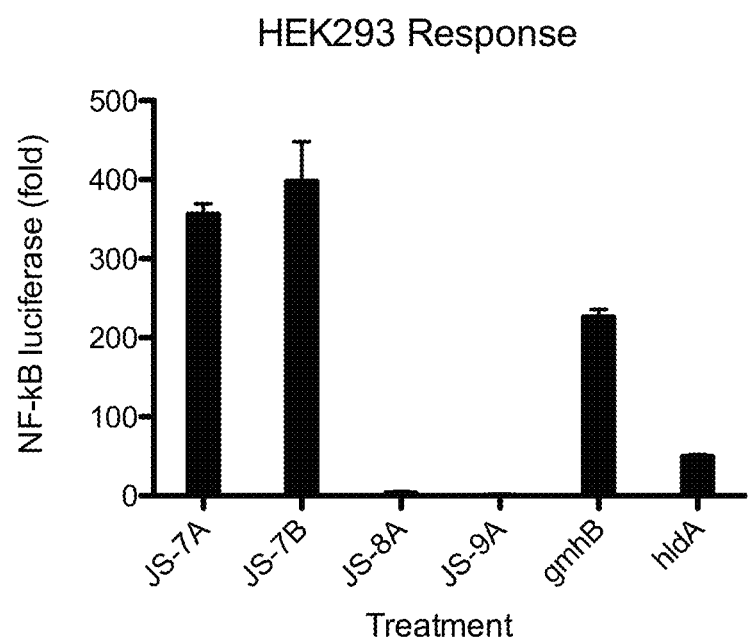
FIG. 7: Effects of compounds/products according to the invention on HEK 293T cells encoding an NF-κB-driven luciferase reporter gene. HEK 293T cells were transfected with a plasmid encoding an NF-κB-driven luciferase reporter. After 24 hours, cells were stimulated for 20 minutes in permeabilization buffer (5 μg/mL digitonin) in the presence of culture supernatant from N. meningitidis mutants with (gmhB) or without (hldA) HBP or 20 μg/mL of synthetic compound according to the invention. Treatment was removed; cells were washed and incubated for 3.5 hours in complete medium. A luciferase assay was then performed. The results are mean of technical triplicates.

HMP-β JS-7 can immunomodulate via NF-κB stimulation in vitro. Effects of compounds/products according to the invention on HEK 293T cells encoding an NF-κB-driven luciferase reporter gene. HEK 293T cells were transfected with a plasmid encoding an NF-κB-driven luciferase reporter. After 24 hours, cells were stimulated for 20 minutes in permeabilization buffer (5 μg/mL digitonin) in the presence of culture supernatant from N. meningitidis mutants with (gmhB) or without (hldA) HBP or 20 μg/mL of synthetic compound according to the invention. Treatment was removed; cells were washed and incubated for 3.5 hours in complete medium. A luciferase assay was then performed. The results obtained are illustrated in FIG. 7; they are mean of technical triplicates.

Example 2

Figure 8:
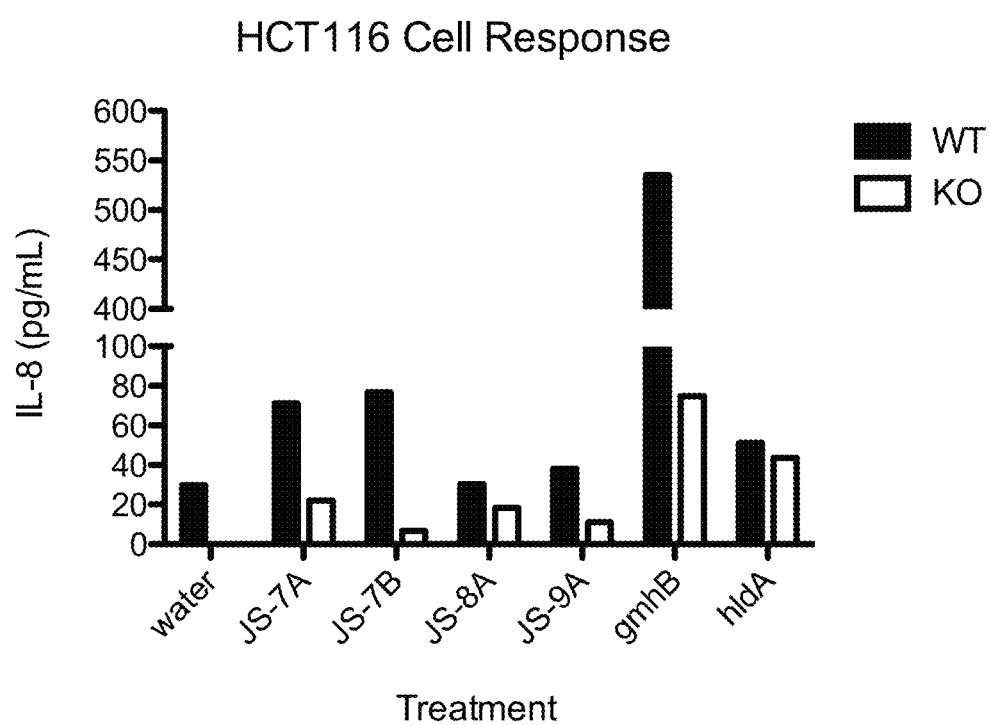
FIG. 8: Stimulation of human colonic epithelial cells by compounds/products according to the invention. Human colonic epithelial cells (HCT 116) that were either wild type (WT) or deficient in TIFA protein expression (knockout, KO) were stimulated for 20 minutes in permeabilization buffer (5 μg/mL digitonin) in the presence of culture supernatant from N. meningitidis mutants with (gmhB) or without (hldA) HBP or 10 μg/mL of synthetic compound according to the invention. Treatment was removed, cells were washed, and cells were incubated for 6 hours in complete media and IL-8 levels in culture supernatants was measured by ELISA. The results are mean of technical duplicates.

HMP-β JS-7 can drive cytokine expression in vitro. Stimulation of human colonic epithelial cells by compounds/products according to the invention. Human colonic epithelial cells (HCT 116) that were either wild type (WT) or deficient in TIFA protein expression (knockout, KO) were stimulated for 20 minutes in permeabilization buffer (5 μg/mL digitonin) in the presence of culture supernatant from N. meningitidis mutants with (gmhB) or without (hldA) HBP or 10 μg/mL of synthetic compound according to the invention. Treatment was removed, cells were washed, and cells were incubated for 6 hours in complete media and IL-8 levels in culture supernatants was measured by ELISA. The results obtained are illustrated in FIG. 8; they are mean of technical duplicates.

Example 3

Figure 9:
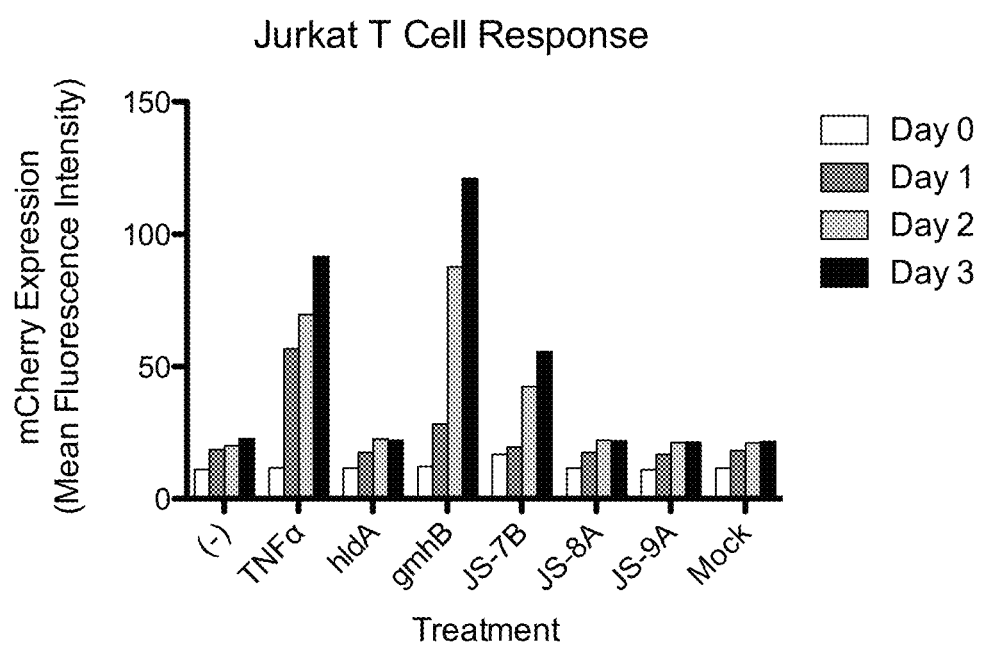
FIG. 9: Stimulation of HIV proviral expression in Jurkat CD4+ T cells. Jurkat CD4+ T cell line containing latent recombinant HIV encoding mCherry fluorescent protein were exposed to the cytokine TNFα, culture supernatant from N. meningitidis mutants with (gmhB) or without (hldA) HBP, or 20 μg/mL of synthetic compound according to the invention. Expression of mCherry fluorescence was detected by flow cytometry immediately (Day 0) or after 1, 2 or 3 days, as indicated. Mock samples were exposed to buffer alone without added stimulatory agents.

Stimulation of HIV proviral expression in Jurkat CD4+ T cells. Jurkat CD4+ T cell line containing latent recombinant HIV encoding mCherry fluorescent protein were exposed to the cytokine TNFα, culture supernatant from N. meningitidis mutants with (gmhB) or without (hldA) HBP, or 20 μg/mL of synthetic compound according to the invention. Expression of mCherry fluorescence was detected by flow cytometry immediately (Day 0) or after 1, 2 or 3 days, as indicated. Mock samples were exposed to buffer alone without added stimulatory agents. The results obtained are illustrated in FIG. 9.

Example 4

Figure 10:
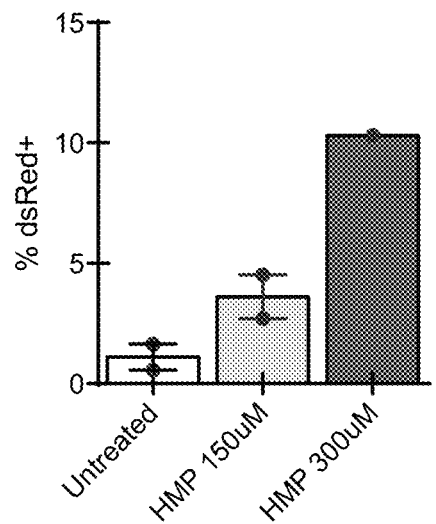
FIG. 10: Stimulation of HIV proviral expression in Jurkat CD4+ T cells. Jurkat CD4+ T cell line containing latent recombinant HIV encoding dsRed fluorescent protein were exposed to 150 μM or 300 μM of synthetic compound according to the invention for 24 hours. Expression of dsRed fluorescence was detected by flow cytometry immediately (Day 0) or after 24 hours. Untreated sample was exposed to buffer alone without added stimulatory agents.

HMP-β JS-7 can drive HIV out of latency in vitro. Stimulation of HIV proviral expression in Jurkat CD4+ T cells. Jurkat CD4+ T cell line containing latent recombinant HIV encoding dsRed fluorescent protein were exposed to 150 or 300 μM of HMP-β JS-7. Expression of dsRed fluorescence was detected by flow cytometry immediately at 24 hours. Untreated samples were exposed to buffer alone without added stimulatory agents. The results obtained are illustrated in FIG. 10.

Example 5

Figure 11:
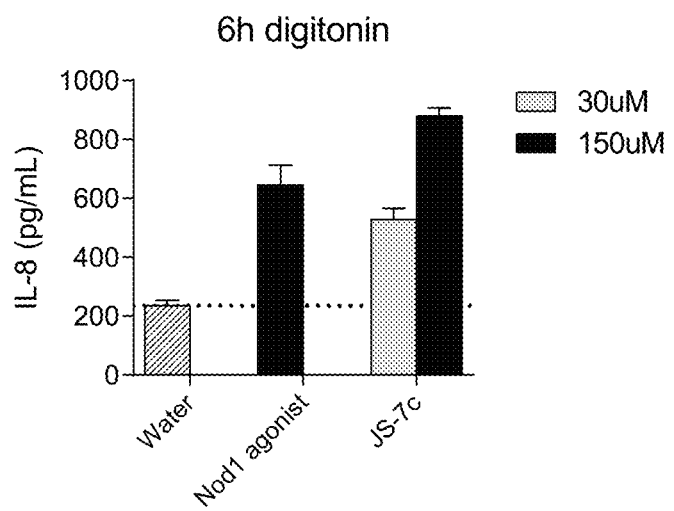
FIG. 11: Stimulation of human macrophages by compounds/products according to the invention. Human macrophage cells (THP-1) were stimulated for 20 minutes in permeabilization buffer (5 μg/mL digitonin) in the presence of water, 39.8 μM of the Nod1 agonist C12-iE-DAP (which stimulates in a TIFA-independent manner), or either 30 μM or 150 μM of synthetic compound according to the invention. Treatment was removed, cells were washed, and cells were incubated for 6 hours in complete media before the IL-8 levels in culture supernatants were measured by ELISA. The results are the mean and standard error of the mean of three technical replicates. Nod1 agonist: C12-iE-DAP (20 μg/mL, 39.8 μM); JS-7: JS-7:D-glycero-β-D-manno-heptose-phosphate.

HMP-8 JS-7 can drive cytokine expression in vitro. Stimulation of human macrophages by compounds/products according to the invention. Human macrophage cells (THP-1) were stimulated for 20 minutes in permeabilization buffer (5 μg/mL digitonin) in the presence of water, 39.8 μM of the Nod1 agonist C12-iE-DAP (which stimulates in a TIFA-independent manner), or either 30 μM or 150 μM of synthetic compound according to the invention. Treatment was removed, cells were washed, and cells were incubated for 6 hours in complete media before the IL-8 levels in culture supernatants were measured by ELISA (FIG. 11). The results are the mean and standard error of the mean of three technical replicates. Nod1 agonist: C12-iE-DAP (20 μg/mL, 39.8 μM); JS-7: JS-7:D-glycero-β-D-manno-heptose-phosphate.

Example 6

Figure 12:
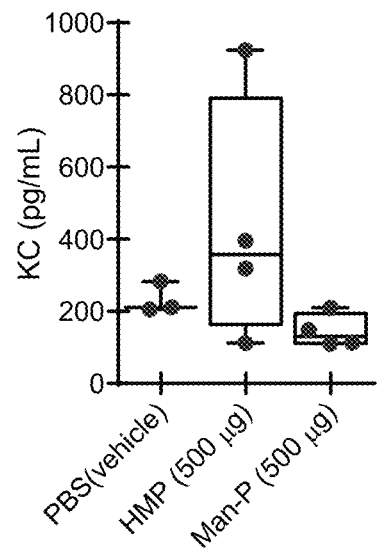
FIG. 12: In vivo administration of HMP-β (JS7) compared to Man-1β-P (JS9). Administered PBS (vehicle control), HMP, or Man-1β-P intraperitoneally, 500 μg/mouse (HMP and MP) in 0.5 mL, assessed serum KC levels 3 h post-injection. Data are presented as box and whisker plots, min/max. Kruskal-Wallis (1way ANOVA, non-parametric), compare against PB.
Figure 13:
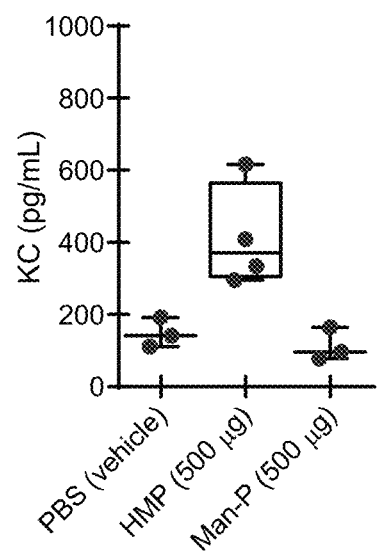
FIG. 13: In vivo administration of HMP-β (JS7) compared to Man-1β-P (JS9). Administered PBS (vehicle control), HMP, or Man-1β-P intravenously, 500 μg/mouse (HMP and MP) in 0.1 mL, assessed serum KC levels 1 h post-injection. Data are presented as box and whisker plots, min/max. Kruskal-Wallis (1way ANOVA, non-parametric), compare against PBS.

HMP-β JS7 alone induces cytokine production in vivo. In vivo administration of HMP-β JS7 (500 μg) via IP (FIG. 12) and IV (FIG. 13) routes induced serum KC levels when compared to the vehicle PBS and the control JS9 Man-1β-P (500 μg).

Example 7

Figure 14:
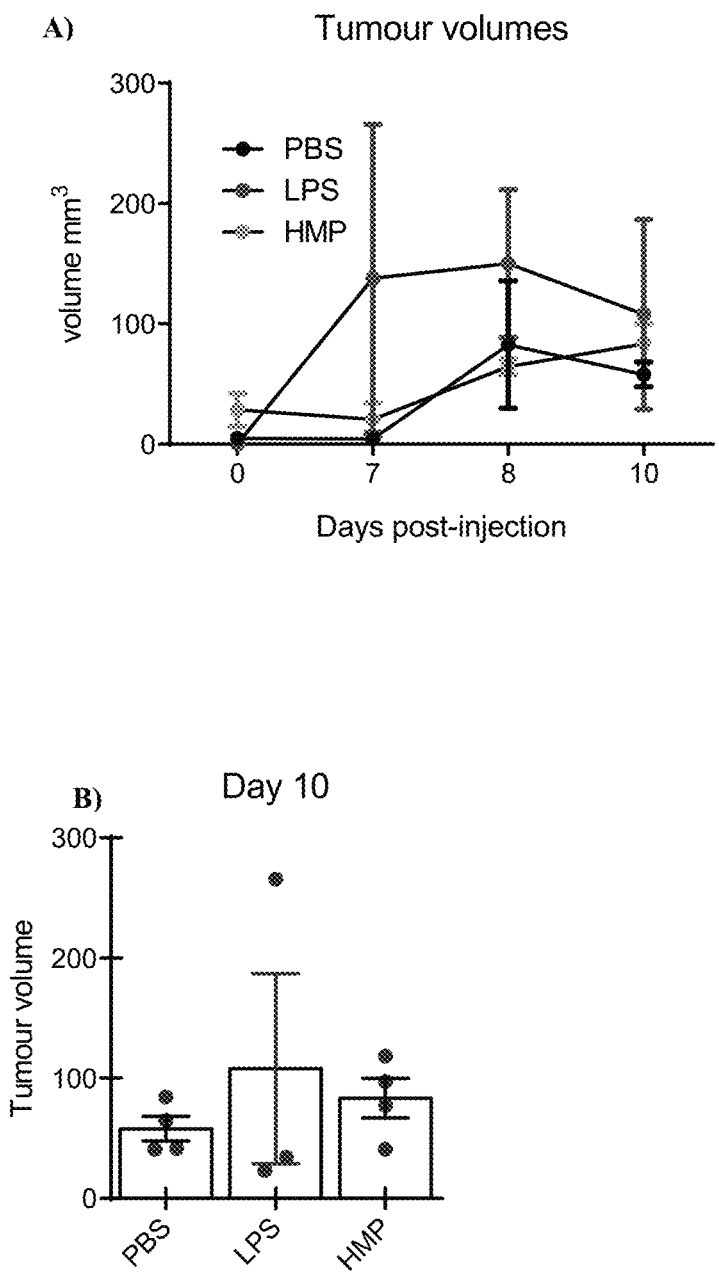
FIG. 14: Cancer tumor cell targeting. BALB/c mice were injected subcutaneously with $10^5$ cells CT26 cells (colon carcinoma from BALB/c mice) in the flank in a volume of 100 μL.
Figure 14:
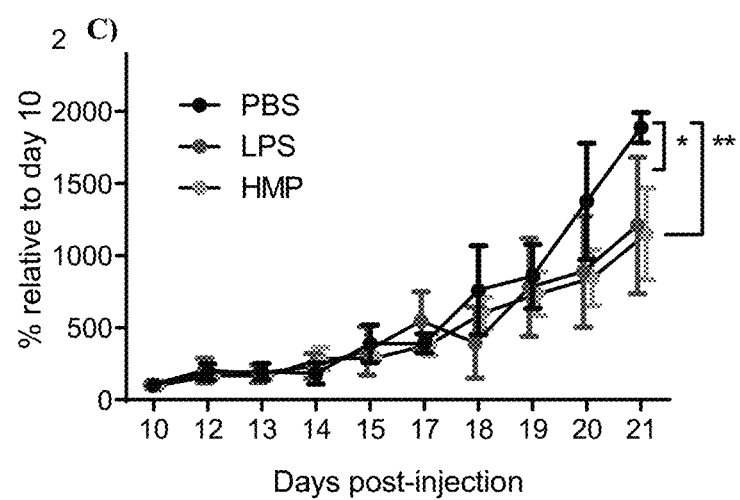

HMP can reduce increasing tumour volumes in a cancer model. BALB/c mice were injected subcutaneously with $10^5$ cells CT26 cells (colon carcinoma from BALB/c mice) in the flank in a volume of 100 μL. Tumours were measured daily over time. Once all mice within the group grew a measurable tumour (FIG. 14a), they were injected intraperitoneally with either LPS (lx at 3 mg/kg), HMP (200 μg per day for 3 days in a row at D10, D11, D12), or PBS (lx per day for 3 days in a row). One mouse from the LPS group was removed since no tumour ever became apparent. Prior to treatment, tumour sizes were not statistically different across mice allocated to different treatment groups (FIG. 14b). The change in tumour volume relative to day 10 was measured for each of the treatment groups and it was found that LPS ($p<0.05$) and HMP-β JS-7 ($p<0.01$) significantly reduced the rate of tumour growth over an 11 day period (FIG. 14c).

Example 8

Figure 15:
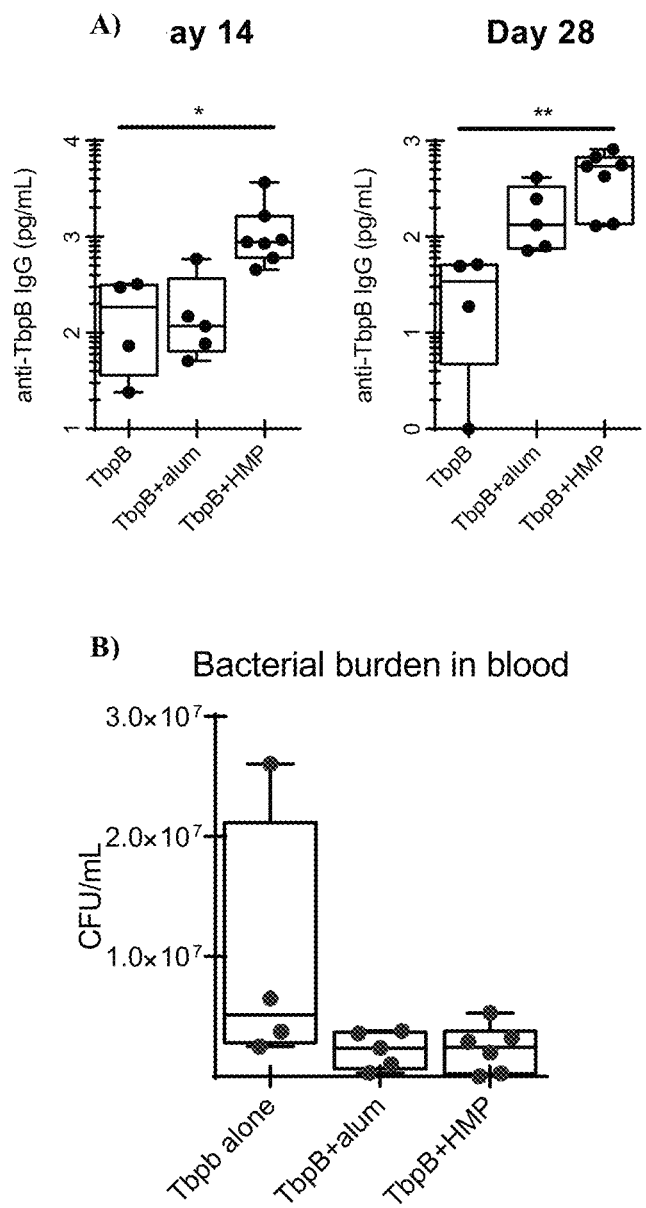
FIG. 15: 6-week-old male C57BL/6NCrl mice were immunized with TbpB originating from group B *N. meningitidis*, purified from recombinant *E. coli*. All groups were immunized with 25 μg of TbpB with or without adjuvant, in a total volume of 30 μL intramuscularly: TbpB alone, TbpB+alum, and TbpB+HMP-β JS-7 (200 μg). Three doses were given: D0, D21, and D28. Serum was collected at D0 prior to immunization, D14, D28, and D35 and then examined by ELISA for IgG titers to TbpB (FIG. 15a). Mice were challenged on D36 with $5 \times 10^7$ of *N. meningitidis* strain expressing the homologous TbpB. Mice were injected with human transferrin (200 μL of 8 mg/mL) as this is critical for the development of sepsis in this model. Mice were monitored at the 1 h, 12 h, 18 h, 24 h, and 36 h time points. At 1 h, blood was collected to enumerate CFUs (FIG. 15b). Clinical scores were collected at 12 h post challenge (FIG. 15c).
Figure 15:
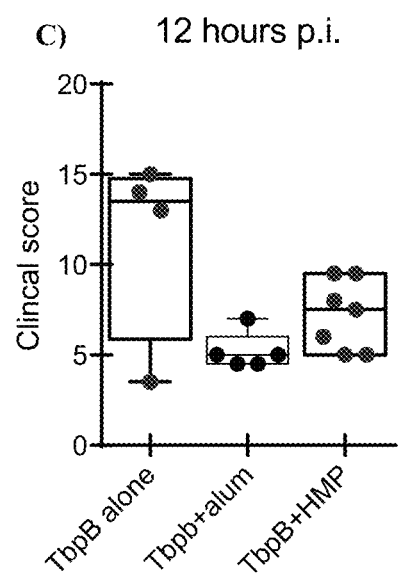

HMP-β JS-7 can act as an adjuvant. 6-week-old male C57BL/6NCrl mice were immunized with TbpB originating from group B *N. meningitidis*, purified from recombinant *E. coli*. All groups were immunized with 25 μg of TbpB with or without adjuvant, in a total volume of 30 μL intramuscularly TbpB alone, TbpB+alum, and TbpB+HMP-β JS-7 (200 μg). Three doses were given: D0, D21, D28. Serum was collected at D0 prior to immunization, D14, D28, and D35 and then examined by ELISA for IgG titers to TbpB. HMP-β JS-7 co-administration with the antigen resulted in titers that were significantly higher than administration of TbpB alone and greater than observed with alum as the adjuvant (FIG. 15a). Mice were challenged on D36 with $5\times10^7$ of *N. meningitidis* strain expressing the homologous TbpB. Mice were injected with human transferrin (200 μL of 8 mg/mL) as this is critical for the development of sepsis in this model. Mice were monitored at the 1 h, 12 h, 18 h, 24 h, and 36 h time points. At 1 h, blood was collected to enumerate CFUs. Clinical scores and weights for mice were collected at all time points. Bacterial burden was reduced and clinical scores were lower for mice that received TbpB antigen along with alum or HMP-β JS-7, consistent with the elevated anti-TbpB titers. FIG. 15b bacterial burden CFU in blood and FIG. 15c clinical scores 12 h post challenge.

The scope of the claims should not be limited by the preferred embodiments set forth in the examples, but should be given the broadest interpretation consistent with the description as a whole.

The present description refers to a number of documents, the content of which is herein incorporated by reference in their entirety.

REFERENCES

1. Medzhitov R. *Immunity* (2009) 30, 766-775.
2. Medzhitov R. *Nature* (2007) 449, 819-826.
3. Robinson J. A. and Moehle K. *Pure Appl. Chem.* (2014) 86(10), 1483-1538.
4. Gaudet R. G. et al. *Science* (2015) 348(6240), 1251-1255.
5. Malott R. J. *PNAS* (2013) 110(25), 10234-10239.
6. Zamyatina et al. *Carbohydr. Res.* (2003) 338, 2571-2589.

The invention claimed is:

1. A method for treating Human Immunodeficiency Virus (HIV) infection in a subject being treated with a therapeutic agent for HIV, comprising administering to the subject being treated with a therapeutic agent for HIV an effective amount of D-glycero-D-manno-heptopyranose 1β-phosphate (HMP-β).

2. The method according to claim 1, wherein the administration of HMP-β induces HIV gene expression from latently infected cells.

3. A method for inducing Human Immunodeficiency Virus (HIV) gene expression from latently infected cells comprising administering to the latently infected cells an effective amount of D-glycero-D-manno-heptopyrano se 1β-phosphate (HMP-β).

* * * * *